United States Patent
Haase et al.

(10) Patent No.: US 10,010,667 B2
(45) Date of Patent: Jul. 3, 2018

(54) IMPLANTABLE INFUSION DEVICE INCLUDING ANTI-SEALING RESERVOIR

(75) Inventors: James M. Haase, Maplewood, MN (US); Ronald L. Mezera, Lake Elmo, MN (US); John M. Gray, Brooklyn Park, MN (US); Nicholas R. Whitehead, Hopkins, MN (US)

(73) Assignee: Medtronic, Inc., Minneapolis, MN (US)

( * ) Notice: Subject to any disclaimer, the term of this patent is extended or adjusted under 35 U.S.C. 154(b) by 1360 days.

(21) Appl. No.: 13/275,690

(22) Filed: Oct. 18, 2011

(65) Prior Publication Data
US 2013/0096537 A1 Apr. 18, 2013

(51) Int. Cl.
*A61M 5/142* (2006.01)
*A61M 5/148* (2006.01)
*A61M 5/145* (2006.01)

(52) U.S. Cl.
CPC .... *A61M 5/14212* (2013.01); *A61M 5/14276* (2013.01); *A61M 5/1483* (2013.01); *A61M 2005/14264* (2013.01); *A61M 2005/14513* (2013.01); *A61M 2205/3341* (2013.01); *A61M 2205/8218* (2013.01)

(58) Field of Classification Search
CPC .......... A61M 5/14276; A61M 5/14244; A61M 31/002; A61M 39/0208; A61M 39/02; A61M 5/14586; A61M 5/14224; A61M 5/142; A61M 5/14212
USPC ........ 604/890.1, 891.1, 288.01, 288.04, 131, 604/151
See application file for complete search history.

(56) References Cited

U.S. PATENT DOCUMENTS

| | | | | |
|---|---|---|---|---|
| 4,193,397 A * | 3/1980 | Tucker et al. | ................ | 604/502 |
| 4,604,090 A * | 8/1986 | Reinicke | ........... | A61M 5/14276 |
| | | | | 128/DIG. 12 |
| 5,514,103 A * | 5/1996 | Srisathapat et al. | .......... | 604/141 |
| 5,976,109 A * | 11/1999 | Heruth | ............... | A61M 5/14276 |
| | | | | 604/140 |
| 6,764,472 B1 * | 7/2004 | Burke | ............... | A61M 5/14276 |
| | | | | 604/288.04 |
| 7,070,577 B1 * | 7/2006 | Haller et al. | .................. | 604/131 |
| 7,108,686 B2 * | 9/2006 | Burke | ............... | A61M 5/14276 |
| | | | | 604/131 |
| 7,867,221 B2 | 1/2011 | Haase | | |
| 2008/0027376 A1 * | 1/2008 | Kriesel | ............. | A61M 5/14244 |
| | | | | 604/84 |
| 2009/0227989 A1 * | 9/2009 | Burke | ............... | A61M 5/14276 |
| | | | | 604/891.1 |
| 2011/0009814 A1 * | 1/2011 | Tsoukalis | .......... | A61M 5/14224 |
| | | | | 604/66 |

(Continued)

*Primary Examiner* — Gerald Landry, II
(74) *Attorney, Agent, or Firm* — Shumaker & Sieffert, P.A.

(57) ABSTRACT

Techniques are disclosed for reducing the accumulation of gases in an implantable infusion device. In one example, an implantable infusion device (IID) includes a housing, an expandable and contractible reservoir, and a standoff member. The expandable and contractible reservoir is configured to store a therapeutic agent and is arranged within the housing. A first end of the reservoir is configured to collapse toward a second end of the reservoir as the reservoir contracts. The standoff member is interposed between the first end and the second end of the reservoir and is configured to hold at least a portion of the first end offset from the second end when the reservoir is in a contracted state.

29 Claims, 6 Drawing Sheets

(56) References Cited

U.S. PATENT DOCUMENTS

| | | | |
|---|---|---|---|
| 2012/0053571 A1* | 3/2012 | Petri | A61M 5/14276 |
| | | | 604/891.1 |
| 2012/0203177 A1* | 8/2012 | Lanier, Jr. | A61M 5/14224 |
| | | | 604/151 |
| 2013/0096503 A1* | 4/2013 | Haase | A61M 5/16809 |
| | | | 604/152 |
| 2013/0158482 A1* | 6/2013 | Davis | A61B 5/150022 |
| | | | 604/173 |
| 2014/0148761 A1* | 5/2014 | Rotem | A61M 5/14593 |
| | | | 604/132 |

* cited by examiner

IMPLANTABLE INFUSION DEVICE INCLUDING ANTI-SEALING RESERVOIR

TECHNICAL FIELD

This disclosure relates to implantable medical devices and, more particularly, to implantable infusion devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic agents, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic agent to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic agent, such as a drug, for delivery to a site in the patient. The fluid reservoir can be self-sealing and accessible through one or more ports. A pump is fluidly coupled to the reservoir for delivering the therapeutic agent to the patient. A catheter provides a pathway for delivering the therapeutic agent from the pump to the delivery site in the patient.

SUMMARY

In general, this disclosure describes techniques for reducing the accumulation of gas in an implantable infusion device. In one example, an implantable infusion device (IID) includes a housing, an expandable and contractible reservoir, and a standoff member. The expandable and contractible reservoir is configured to store a therapeutic agent and is arranged within the housing. A first end of the reservoir is configured to collapse toward a second end of the reservoir as the reservoir contracts. The standoff member is interposed between the first end and the second end of the reservoir. The standoff member is configured to hold at least a portion of the first end offset from the second end when the reservoir is in a contracted state.

In another example, an IID includes a housing and an expandable and contractible reservoir. The expandable and contractible reservoir is configured to store a therapeutic agent and is arranged within the housing. The reservoir includes a first end connected to the housing, a substantially closed second end including a protrusion protruding toward the first end, and a side connecting the first and the second ends to form a reservoir chamber within which the reservoir stores the therapeutic agent. The second end of the reservoir is configured to collapse toward the first end as the reservoir contracts. The protrusion is configured to hold at least a portion of the second end offset from the first end when the reservoir is in a contracted state.

In another example, a system includes a programmer, an IID, and a catheter. The IID includes a housing and an expandable and contractible reservoir. The expandable and contractible reservoir is configured to store a therapeutic agent and is arranged within the housing. The reservoir includes a first end, a substantially closed second end, and a side. The first end is connected to the housing. The substantially closed second end includes a protrusion protruding toward the first end. The side connects the first and the second ends to form a reservoir chamber within which the reservoir stores the therapeutic agent. The second end of the reservoir is configured to collapse toward the first end as the reservoir contracts. The protrusion is configured to hold at least a portion of the second end offset from the first end when the reservoir is in a contracted state. The catheter is connected to and configured to deliver the therapeutic agent from the reservoir to a site within a patient.

In another example, a reservoir configured to store a therapeutic agent in an IID includes a first end, a second substantially closed planar end, and a corrugated annular side. The first end includes a ring-shape that forms an opening toward a center of the first end. The second substantially closed planar end includes a protrusion protruding toward the first end. The corrugated annular side is substantially perpendicular to and connects the first and the second ends to form a cylindrical chamber within which the reservoir stores the therapeutic agent. The corrugated annular side is configured to expand and contract to change a distance between the first end and the second end of the reservoir. The protrusion is configured to hold at least a portion of the second end offset from the first end when the reservoir is in a contracted state.

In another example, an implantable infusion device (IID) includes a housing, an expandable and contractible reservoir, and standoff means. The expandable and contractible reservoir is configured to store a therapeutic agent and is arranged within the housing. A first end of the reservoir is configured to collapse toward a second end of the reservoir as the reservoir contracts. The standoff means is interposed between the first end and the second end of the reservoir. The standoff means is for holding at least a portion of the first end offset from the second end when the reservoir is in a contracted state.

The details of one or more examples disclosed herein are set forth in the accompanying drawings and the description below. Other features, objects, and advantages will be apparent from the description and drawings, and from the claims.

DETAILED DESCRIPTION

Figure 1:
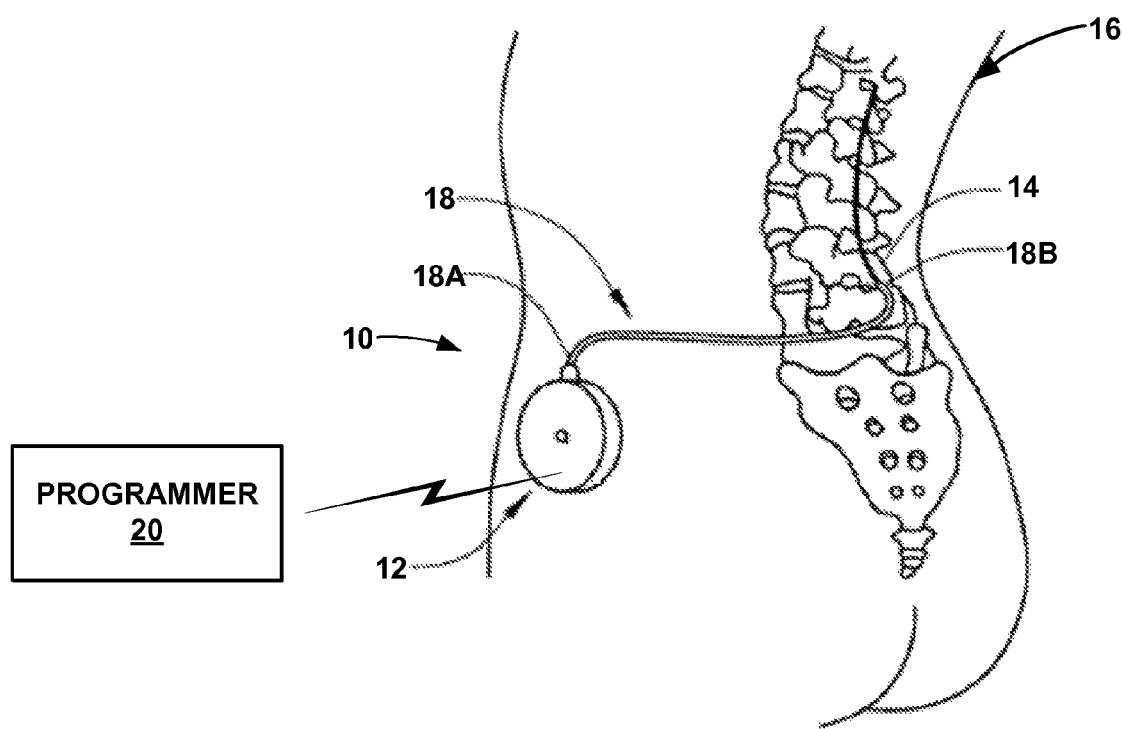
FIG. 1 is a conceptual diagram illustrating an example of a fluid delivery system including an implantable infusion device configured to deliver a therapeutic agent to a patient via a catheter.

The presence of gas in some parts of an implantable infusion device (IID), e.g. a drug infusion pump, may affect the operation of the device and the capacity of the device to deliver therapy to a patient. IIDs may be subject to accumulation of gases in the fluid path of the device, e.g. between a fluid reservoir and the pump of the device and/or from the pump to the distal end of the catheter, from which a therapeutic agent is dispensed to a patient. The accumulation of gas in an IID may result in disruptions and inaccuracies of the intended dispense profile by which the device is intended to deliver the therapeutic agent to the patient. To improve stable performance over the life of the IID, therefore, it may be important to limit the volume of gas in the fluid path. Among other factors, gas volume in the fluid path of an IID may depend on the initial conditions of the device, e.g., following a first fluid path purge and prime procedure, the introduction of gases via refill procedures, either dissolved in the liquid and subsequently comes out of solution or introduced as gas bubbles, and mass transfer effects through permeable device components.

The fluid path of an IID, at least with respect to the therapeutic agent or agents delivered by the device to a patient, generally includes a fluid path that is "upstream" of the pump of the device and the path from the pump, "downstream" through and to the end of a catheter from which one or more agents are delivered to a target location within a patient. The relative terms "upstream" and "downstream," as used in this disclosure may refer to locations within or portions of an IID relative to a pumping mechanism of the device and in the direction of the fluid flow through the device. For example, upstream of the pump includes any components or functions that occur before and up to a fluid reaching an inlet to the pump, while downstream of the pump describes locations from the pump outlet to a distal end of the catheter of the IID. In one example IID, upstream locations of the fluid path include the refill port into the device reservoir and from the reservoir to the inlet of the pumping mechanism. Downstream locations may include locations from the pump outlet through channels in the IID and out of the device through and to the distal end of the catheter connected to the IID.

In some IID designs, the potentially deleterious effect of gas accumulation within the device may be greater upstream of and/or within the pumping mechanism. For example, gas accumulation within the stroke chamber of a piston pump may adversely affect the operation of the pump, and, in some cases, reduce the ability of the pump to accurately deliver metered fluid doses to a patient. Additionally, gases that accumulate within the reservoir upstream of the pump may adversely affect some therapeutic agents stored within the reservoir over time. In view of the foregoing effects of and challenges related to gas accumulation within an IID, examples according to this disclosure include a structure that facilitates rapid and improved purging of the fluid path of an IID at the point of manufacture, as well as during subsequent purge and prime procedures, e.g. during a refill, without adding significant dead volume to the device fluid path.

FIG. 1 is a conceptual diagram illustrating an example of a therapy system 10, which includes IID 12, catheter 18, and external programmer 20. IID 12 is connected to catheter 18 to deliver at least one therapeutic agent, e.g. a pharmaceutical agent, pain relieving agent, anti-inflammatory agent, gene therapy agent, or the like, to a target site within patient 16. IID 12 includes an outer housing that, in some examples, is constructed of a biocompatible material that resists corrosion and degradation from bodily fluids including, e.g., titanium or biologically inert polymers. IID 12 may be implanted within a subcutaneous pocket relatively close to the therapy delivery site. For example, in the example shown in FIG. 1, IID 12 is implanted within an abdomen of patient 16. In other examples, IID 12 may be implanted within other suitable sites within patient 16, which may depend, for example, on the target site within patient 16 for the delivery of the therapeutic agent. In still other examples, IID 12 may be external to patient 16 with a percutaneous catheter connected between IID 12 and the target delivery site within patient 16.

IID 12 delivers a therapeutic agent from a reservoir (not shown) to patient 16 through catheter 18 from proximal end 18A coupled to IID 12 to distal end 18B located proximate to the target site. Example therapeutic agents that may be delivered by IID 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IID 12 as needed, such as to provide or retrieve therapy information or control aspects of therapy delivery (e.g., modify the therapy parameters such as rate or timing of delivery, turn IID 12 on or off, and so forth) from IID 12 to patient 16.

Catheter 18 may be coupled to IID 12 either directly or with the aid of a catheter extension (not shown in FIG. 1). In the example shown in FIG. 1, catheter 18 traverses from the implant site of IID 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IID 12 delivers a therapeutic agent through catheter 18 to targets proximate to spinal cord 14.

IID 12 can be configured for intrathecal drug delivery into the intrathecal space, as well as epidural delivery into the epidural space, both of which surround spinal cord 14. In some examples, multiple catheters may be coupled to IID 12 to target the same or different nerve or other tissue sites within patient 16, or catheter 18 may include multiple lumens to deliver multiple therapeutic agents to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IID 12 by wireless telemetry. For example, programmer 20 may be a clinician programmer that the clinician uses to communicate with IID 12 and program therapy delivered by the IID. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IID 12. Programmer 20 may be a handheld or other dedicated computing device, or a larger workstation or a separate application within another multi-function device.

In examples according to this disclosure, IID 12 includes an expandable and contractible reservoir, the volume of which generally varies with the volume of therapeutic fluid stored in the reservoir. In one example, the reservoir includes a bellows with a generally cylindrical shape including a closed end, e.g. a bottom and an annular side wall with a plurality of corrugations. The end opposite the closed end, e.g. the top of the reservoir may be partially or completely open and may be connected to a bulkhead of the IID, thereby forming an enclosed chamber within which one or more therapeutic agents may be stored. The reservoir is configured to expand with larger volumes of fluid as the corrugations in the annular side wall spread out such that the closed end moves away from the bulkhead. Conversely, the reservoir is configured to collapse with smaller volumes of fluid as the corrugations in the annular side wall contract such that the closed end moves toward the bulkhead. IID 12 includes a standoff member that is interposed between the bulkhead and the closed end of the reservoir, which is configured to hold at least a portion of the closed end offset from the bulkhead when the reservoir is in a contracted state. The standoff member creates an open space in the reservoir, which is maintained during a purge and prime and/or refill procedure and which defines a fluid path between an inlet of the reservoir from a refill port to an inlet of the pump of the IID. The open fluid path maintained by the standoff member facilitates purging gases from the IID downstream of and within the pump during an initial purge and prime procedure following manufacture of the device and during subsequent refill procedures.

Figure 2A:
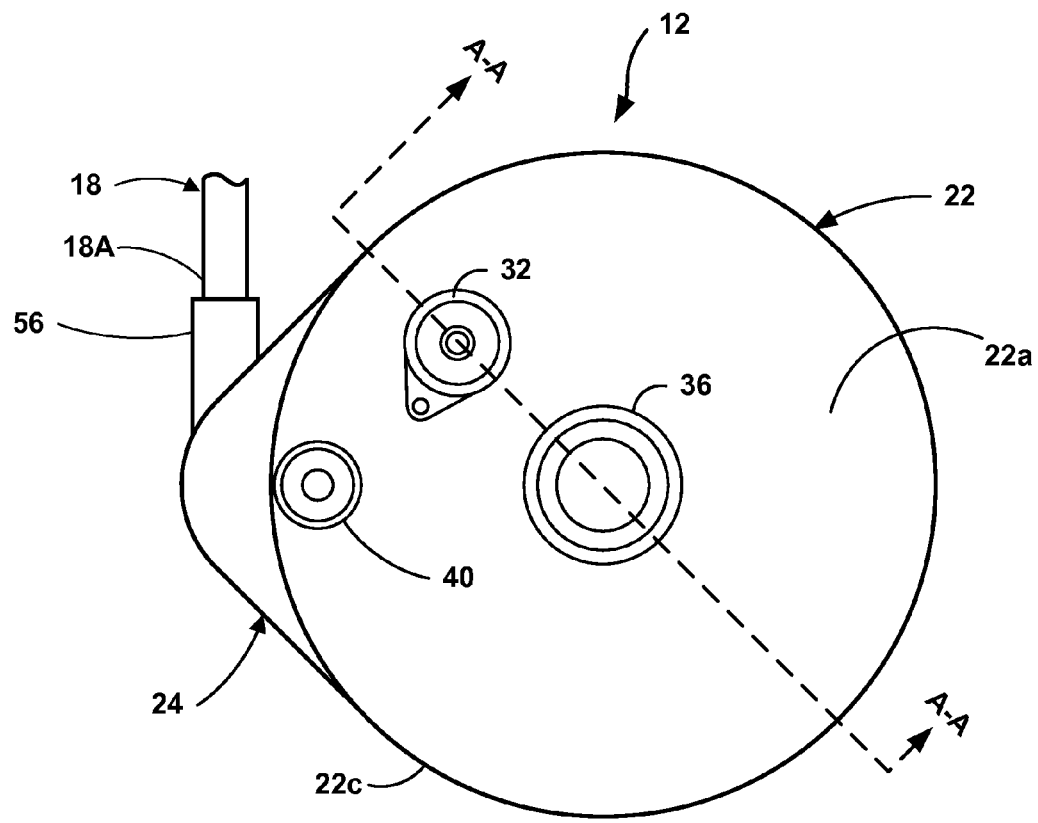
FIG. 2A is a plan view illustrating an example configuration of the implantable infusion device of FIG. 1.
Figure 2B:
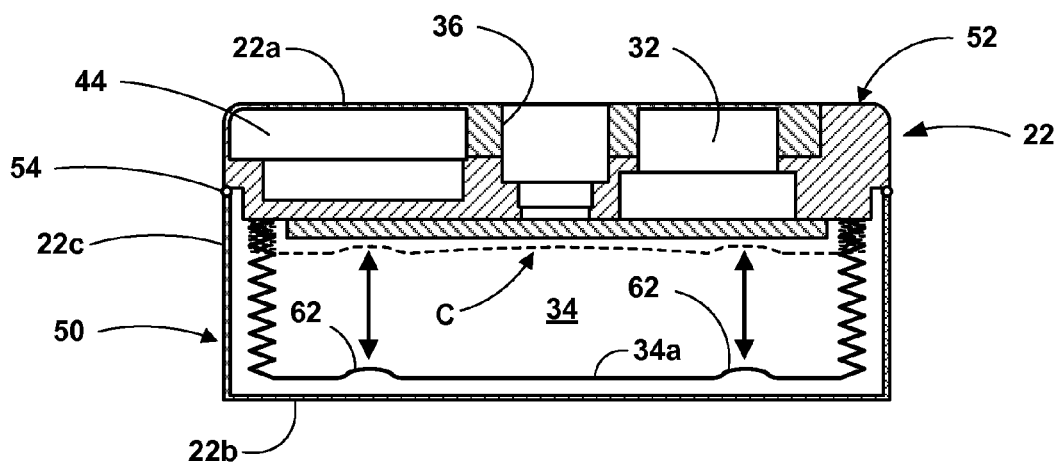
FIG. 2B is a cross-sectional side view of the example implantable infusion device of FIG. 2A cut along the section line A-A of FIG. 2A.

FIGS. 2A and 2B illustrate an example configuration of IID 12 including housing 22, header 24, pump 32, and reservoir 34, refill port 36, catheter access port (CAP) 40, and power source 44. FIG. 2A is a plan view of IID 12 and FIG. 2B is a section view of IID 12 cut along section line A-A in FIG. 2A. In FIGS. 2A and 2B, housing 22 of IID 12 is generally cylindrical, including two circular ends 22a, 22b (only one of which is visible in the view of FIG. 2A) connected to one another by annular wall 22c. Housing 22 is divided into two parts, which include shield 50 and bulkhead 52. Shield 50 and bulkhead 52 of housing 22 are connected at seam 54. In one example, seam 54 includes a weld joint that is configured to join shield 50 and bulkhead 52 such that the interior of IID 12 is hermetically sealed from the outside. Housing may be constructed from biocompatible materials that resist corrosion and degradation from bodily fluids including, e.g., titanium or biologically inert polymers. Housing may be fabricated using a variety of known solid material manufacturing techniques, including, e.g. pressing, casting, molding, or any one or more of various material removal processes, including, e.g., milling, turning, grinding, electrical discharge machining (EDM), or laser or torch cutting. For example, shield 50 may be pressed from sheet stock of a metal or metal alloy, e.g. a titanium alloy, while bulkhead 52 is machined from stock piece of a similar or different material. In another example in which part or all of housing 22 is fabricated from a plastic, shield 50 and/or bulkhead 52 may be manufactured using injection molding techniques.

In one example, shield 50 is a thin wall enclosure that receives and surrounds reservoir 34 of IID 12 (see FIG. 3B). The space between the inner surfaces of the walls of shield 50 and the reservoir of IID 12 defines a chamber within which a propellant gas is held at pressure. The propellant gas in the gas chamber within shield 50 is employed to regulate the pressure within the reservoir of IID 12. Bulkhead 52 houses a number of components of IID 12 including, e.g., control electronics, e.g. processor(s), memory, and telemetry, as well as fluid delivery pump 32, power source 44, and one or more sensors.

Header 24 includes a catheter junction (not shown) and is connected to housing 22 of IID 12 generally along a portion of annular side wall 22c. Header 24 forms the connection between IID 12 and a catheter through which the device delivers a therapeutic agent to a patient, e.g. catheter 18 of FIG. 1. Tubes and/or passages in header 24 and bulkhead 52 provide a fluid connection between the outlet of fluid delivery pump 32 of IID 12 and catheter 18, which is either directly connected or indirectly connected via extension 56.

As noted above, housing 22 of IID 12 is generally cylindrical, including two circular ends 22a, 22b connected to one another by annular side 22c. In FIG. 2B, shield 50 includes one of the two generally circular ends 22b of housing 22, and bulkhead 52 includes the other circular end 22a of housing 22. Shield 50 also includes a portion of annular side 22c below seam 54 in the view of FIG. 2B, while the remaining portion of annular side 22c of housing 22 is part of bulkhead 52, i.e. above seam 54 in the view of FIG. 2B.

Refill port 36 of IID 12 is arranged in bulkhead 52 near the center of circular wall 22a. Refill port 36 is connected to reservoir 34. Periodically, fluid may need to be supplied percutaneously to the reservoir of IID 12 because all of a therapeutic agent has been or will be delivered to patient 16, or because a clinician wishes to replace an existing fluid with a different fluid or similar fluid with different concentrations of therapeutic ingredients. Refill port 36 can therefore comprise a self-sealing membrane, or septum to prevent loss of therapeutic agent delivered to the reservoir via refill port 36. For example, after a percutaneous delivery system, e.g., a hypodermic needle, penetrates the membrane of refill port 36, the membrane may seal shut when the needle is removed from refill port 36.

Catheter access port 40 is arranged in bulkhead 52 of IID 12 near the perimeter of circular wall 22a. Catheter access port 40 is connected to internal tubing and/or channels in bulkhead 52 and from there to a delivery catheter that is connected to IID 12 via catheter junction 56 of header 24. Clinicians or other users may access a catheter connected to IID 12 directly via catheter access port 40, e.g., to flush the catheter with saline, deliver a therapeutic agent directly to the patient via the catheter, or in the process of executing bridging bolus.

During operation of IID 12, the device controls fluid delivery pump 32 with the aid of instructions associated with program information, e.g. information stored in memory of the device, to deliver a therapeutic agent to patient 16 via catheter 18. Instructions executed by IID 12 may, for example, define therapy programs that specify the dose of therapeutic agent that is delivered to a target tissue site within patient 16 from reservoir 30 via catheter 18. The programs may further specify a schedule of different therapeutic agent rates and/or other parameters by which IID 12 delivers therapy to patient 16.

Fluid delivery pump 32 draws fluid from reservoir 34 and pumps the fluid through internal tubing or cavities in bulkhead 52 of housing 22 of IID 12 to catheter 18 through which the fluid is delivered to patient 16 to effect one or more of the treatments described above, e.g. in accordance with a program stored on memory of the IID. Fluid delivery pump 32 can be any mechanism that delivers a therapeutic agent in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26. In various examples, fluid delivery pump 32 may be an axial pump, a centrifugal pump, a pusher plate pump, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

As illustrated in FIG. 2B, reservoir 34 includes an expandable and contractible bellows, the pressure of which is maintained via a propellant, e.g. a propellant gas. The propellant gas acts as a pressure-providing means to the chamber of reservoir 34, which regulates the pressure within the reservoir by applying pressure to the flexible bellows structure to discharge the therapeutic agent stored in the reservoir through internal tubing 38 to fluid delivery pump 32. In one example, the propellant gas is employed to maintain a substantially constant pressure within reservoir 34 in order to deliver the therapeutic agent through tubing or cavities in bulkhead 52 to pump 32 consistently and accurately over time. The propellant gas is held within the chamber surrounding reservoir 34, which is defined by the inner walls of shield 50 of housing 22 of IID 12. The propellant gas used to regulate the pressure of reservoir 34 of IID 12 may be a fluid that is in phase change between a liquid state and a gas state when, e.g., in equilibrium between phases at around 35-37 degrees Celsius which is a common temperature range of the body of patient 16. The propellant gas employed in examples of IID 12 may comprise at least one of butane, perflurohexane, or perfluropentane.

As the volume of therapeutic agent within reservoir 34 changes, the reservoir is configured to expand and contract. The annular side wall of reservoir 34 is corrugated and configured to expand and contract to change a distance between closed end 34a and bulkhead 52. Reservoir 34 may expand and contract during an initial purge and prime procedure after the manufacture of IID 12 or during a refill procedure after the IID has been implanted within a patient. In FIG. 2B, reservoir 34 is illustrated in solid lines in an expanded state and in dashed lines in a contracted state. The expansion and contraction of reservoir 34 may occur, in addition to as a therapeutic agent is delivered to a patient, during an initial purge and prime procedure after IID 12 is manufactured but before it is implanted in a patient, as well as during a refill procedure after implantation. A clinician may access reservoir 34 via refill port 36 in the manner described above and may aspirate the fluid pathways within IID 12 using a needle. Purging and priming reservoir 34 involves the injection or withdrawal of gases and/or fluids via an inlet port in the reservoir connected to refill port 36, as well as an inlet port to pump 32.

In the course of a purge and prime or refill procedure, as reservoir 34 collapses, closed end 34a of the reservoir moves toward bulkhead 52 and tends to bow and form a seal against the surface of the bulkhead toward the center, as indicated by region C of reservoir 34 in the contracted state in FIG. 2B.

As described in more detail with reference to FIG. 3, when reservoir 34 collapses toward and seals against bulkhead 52 in this manner, e.g. during an initial purge and prime procedure or during a refill procedure for IID 12, it can cause gases to become trapped in several locations downstream of and/or within pump 32. In order to reduce the risk of gas accumulation in IID 12, reservoir 34 includes protrusion 62 in closed end 34a of the reservoir, which functions as a standoff member between bulkhead 52 and the closed end of the reservoir to hold at least a portion of the closed end offset from the bulkhead when the reservoir is in a contracted state. Protrusion 62 in closed end 34a of reservoir 34 creates an open space in the reservoir, which is maintained during a purge and prime and/or refill procedure and which defines a fluid path between an inlet of the reservoir, e.g. from refill port 36 to an inlet of pump 32. The open fluid path maintained by protrusion 62 facilitates purging gases from IID 12 downstream of and within pump 32 during an initial purge and prime procedure following manufacture of the device and during subsequent refill procedures. Although the examples disclosed herein describe protrusion 62 in closed end 34a of the reservoir functioning as a standoff member between bulkhead 52 and the closed end of the reservoir when the reservoir is in a contracted state during purge and prime or refill procedures, protrusion 62 also functions as a standoff member between closed end 34a and bulkhead 52 during normal operation of IID 12 as reservoir 34 contracts when the therapeutic agent stored in the reservoir is delivered to patient 16 by pump 32.

Figure 3:
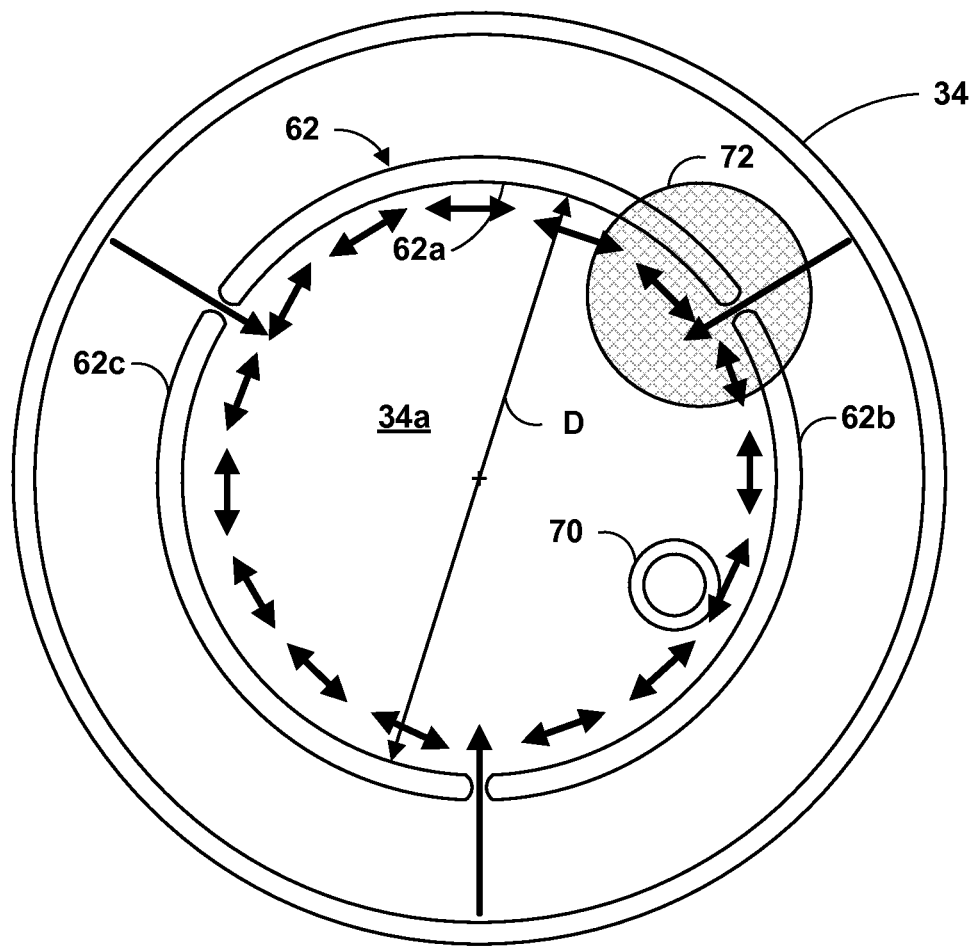
FIG. 3 is a conceptual diagram illustrating a reservoir of an implantable infusion device.

FIG. 3 is a plan view of reservoir 34 of FIGS. 2A and 2B, including protrusion 62 in closed end 34a of the reservoir. Reservoir inlet 70 and pump inlet 72 are also schematically represented in FIG. 3. The flow of fluids and gases into and through reservoir 34 from reservoir inlet 70 to pump inlet 72 are schematically illustrated in FIG. 3 as a number of arrows. The arrows in FIG. 3 are illustrative only and therefore may only represent a portion of the possible flow of gases into and through reservoir 34 under the operating conditions of IID 12 described with reference to FIG. 3. The arrows in FIG. 3 illustrate that protrusion 62 according to this disclosure functions to create a flow path in reservoir 34 through which therapeutic agent and gas may flow from the periphery of the reservoir as well as between reservoir inlet 70 and pump inlet 72.

In one example, reservoir inlet 70 comprises an aperture between refill port 36 of IID 12 (see FIGS. 2A and 2B) and reservoir 34. Reservoir inlet 70 may include an over-pressurization mechanism (OPM) that is designed to reduce the risk of a clinician over-filling reservoir 34. In one example, reservoir inlet 70 includes an OPM including a number of concentric, telescoping cylinders the extension of which actuates a valve between refill port 36 and reservoir 34 that opens when the reservoir is in a partially or completely contracted state and closes when the reservoir is in an expanded state, e.g. full of a therapeutic fluid. In one example, pump inlet 72 may include a filter, which when wetted allows passage of fluid while substantially preventing passage of gases between pump 32 and reservoir 34. Pump inlet 72 is illustrated schematically in FIG. 3 as a circular filter element. In such examples, if the pump filter is wetted with gases trapped within pump 32, e.g., after an initial purge and prime procedure, the gases may not be easily removed from within the pump without evacuating IID 12 of fluids and drying the filter.

As illustrated in FIG. 3, protrusion 62 is ring-shaped and is generally aligned with a center of closed end 34a of reservoir 34. Furthermore, protrusion 62 includes three non-contiguous protrusions 62a, 62b, and 62c that form the ring with a center generally aligned with the center of closed end 34a. In other examples, protrusion 62 or another standoff member in accordance with this disclosure may include more or fewer non-contiguous protrusions, including, e.g. two non-contiguous protrusions that form a ring with a center generally aligned with the center of closed end 34a or four or more non-contiguous protrusions that form a ring with a center generally aligned with the center of closed end 34a.

As illustrated in FIG. 2B, closed end 34a of the reservoir moves toward bulkhead 52 as reservoir 34 collapses and tends to bow and form a seal against the surface of the bulkhead toward the center. When reservoir 34 collapses toward and seals against bulkhead 52 in this manner, a flow path between reservoir inlet 70 and pump inlet 72 and between the periphery of reservoir 34 and reservoir inlet 70 may be closed such that gases may become trapped at the periphery of the reservoir and/or within pump 32. Accumulation of gases within reservoir 34 may adversely affect therapeutic agents stored in the reservoir. For example, the composition of some genetic agents can degrade at a liquid-gas barrier, thereby affecting the efficacy of the agent in treating a condition of the patient within which the IID is implanted. Gas accumulation within pump 32 may adversely affect the operation of the pump, and, in some cases, reduce the ability of the pump to accurately deliver metered fluid doses to a patient. For example, in examples in which pump 32 comprises a piston pump, gas accumulation within the stroke chamber of the piston can cause inaccurate delivery of a fluid therapeutic agent to a patient, because the stroke chamber includes a volume of compressible gas that acts as a pillow against which the piston may cycle without delivering any or while delivering less than the intended amount of therapeutic fluid to the patient.

Protrusion 62, including three non-contiguous protrusions 62a, 62b, and 62c, is configured to create an open space in reservoir 34, which is maintained during a purge and prime and/or refill procedure and which defines a fluid path between reservoir inlet, e.g. from refill port 36 to inlet 72 of pump 32. The open fluid path maintained by protrusion 62 facilitates purging gases from IID 12 upstream of and within pump 32 during an initial purge and prime procedure following manufacture of the device and during subsequent refill procedures. In particular, protrusion 62 functions as a standoff member between closed end 34a of reservoir 34 and bulkhead 52 (see FIG. 2B) to hold at least a portion of the closed end offset from the bulkhead when the reservoir is in a contracted state such that fluids and gases may flow and be purged between reservoir inlet 70 and pump inlet 72, as well as from the periphery of reservoir 34. The spaces between non-contiguous protrusions 62a, 62b, and 62c form a path from the periphery of reservoir 34 radially outward of protrusions 62a, 62b, and 62c, and reservoir and pump inlets 70 and 72, respectively.

Figure 4:
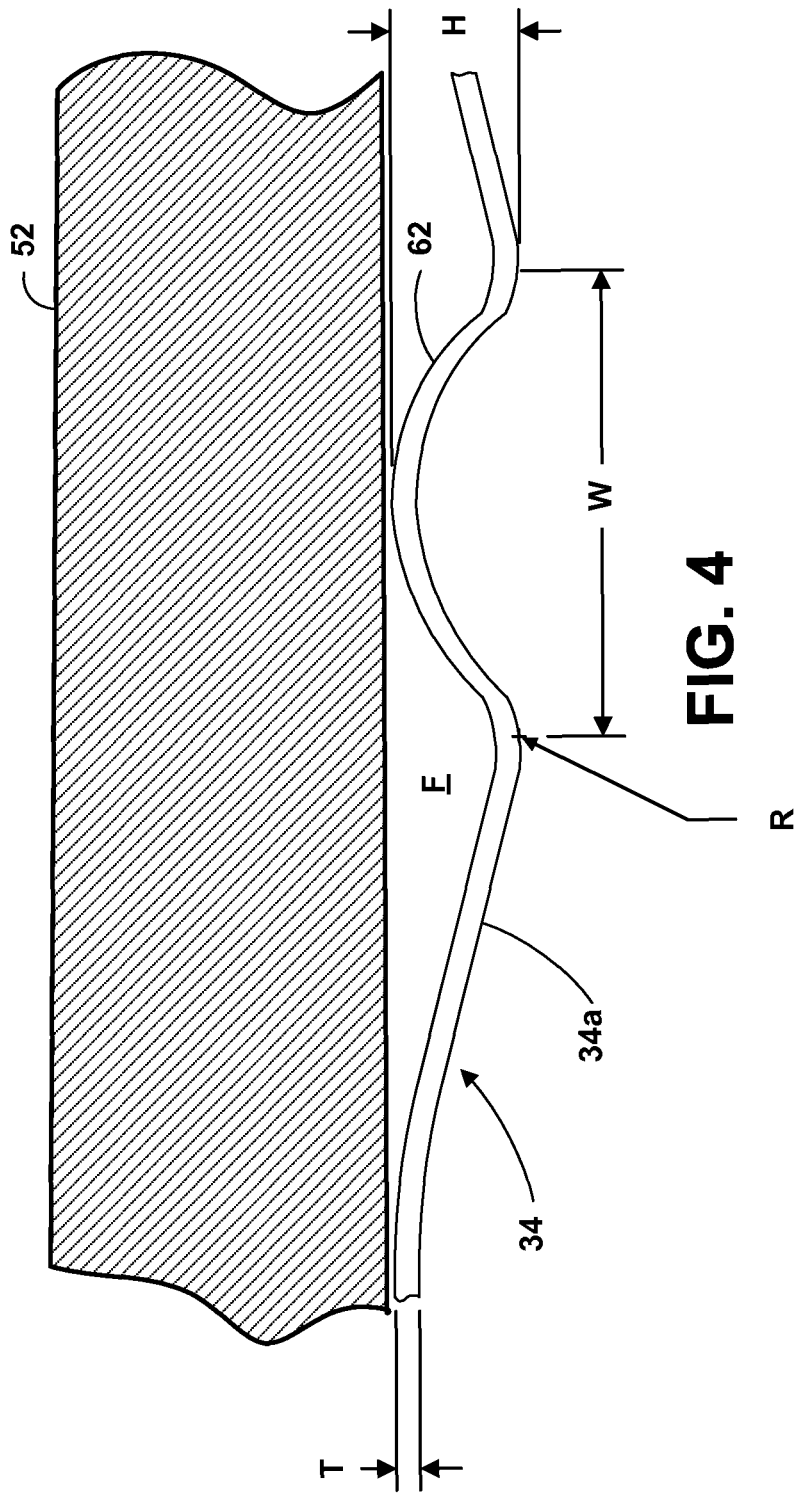
FIG. 4 is a detail view of a reservoir of an implantable infusion device in a contracted state against a bulkhead of the device.

The size, shape, and configuration of protrusion 62 may vary depending on the particular application. Additionally, the size, shape, and configuration of protrusion 62 may depend on constraints of manufacturing, e.g. limits on the size of the feature based on the thickness of closed end 34a of reservoir 34 and mechanical properties of the material from which the reservoir is fabricated. FIG. 4 illustrates the sizing of protrusion 62, as well as the cross-sectional area of the space between closed end 34a of reservoir 34 and bulkhead 52 by protrusion 62. In one example, reservoir 34 is fabricated from titanium and the width, W, of protrusion 62 is selected, at least in part, based on stress thresholds on the titanium which allow plastic deformation while preventing damage or failure of the material in the region of the protrusion.

In one example, the height, H, of protrusion 62 may be determined based on a fluidic resistance of a purging fluid path through IID 12. It is advantageous to have a fast and effective purge, while minimizing the volume of residual therapeutic agent left in reservoir 34, both of which may be a function of the cross-sectional area of the space within reservoir 34 between closed end 34a and bulkhead 52 created by protrusion 62. In one example, a target residual volume in reservoir 34 sets the upper limit of the height of protrusion 62 and a target fluidic resistance of the purge path of IID 12 sets the lower limit. The amount of residual volume of fluid or other therapeutic agent present in reservoir 34 may be important when changing or reducing the concentration of therapeutic agents in the reservoir. For example, when changing a therapeutic agent in reservoir 34 of IID 12, a clinician may rinse the reservoir one or more times with a sterile saline solution. The clinician may then purge IID 12 of the saline, but the residual volume of saline in the reservoir reduces the concentration of a new therapeutic agent that is added by the clinician after rinsing and purging the device. The clinician may perform additional rinses with the new therapeutic agent if the concentration level requirement is greater than what would result from the residual saline and new agent. In one example, a residual volume of approximately 1.4 milliliters may set the upper limit of the height of protrusion 62.

In one example, the target fluidic resistance is based on the cross sectional area of the needle employed during purge and prime, and refill procedures. In one example, the target fluidic resistance is based on a fluid delivery needle larger than or equal to approximately 22 gauge (outer diameter (OD) 0.711 mm) needle. In another example, the target fluidic resistance is based on a fluid delivery needle smaller than or equal to approximately 24 gauge (OD 0.559 mm) needle. The height of protrusion 62 may be selected such that the cross-sectional area of the flow path, which is equivalent to two times the area F shown in FIG. 4 as the therapeutic agent may flow on both sides of protrusion 62, created by the protrusion when pump 32 was in a near empty condition is greater than a cross-sectional area of the fill needle used for the purge or refill procedure. Configuring protrusion 62 in this manner may act to maintain adequate flow through reservoir 34 during a purge and prime or refill procedure.

In some cases, purging IID 12 properly may require maintaining a flow path between reservoir inlet 70 and pump inlet 72. As such, referring again to FIG. 3, the diameter, D, of the ring formed by non-contiguous protrusions 62a, 62b, and 62c may be selected to assure the purge channel created by protrusion 62 crosses both reservoir inlet 70 and pump inlet 72. Thus, in some examples, the diameter of the ring formed by non-contiguous protrusions 62a, 62b, and 62c may vary with the arrangement of reservoir and pump inlets 70 and 72, respectively, within IID 12.

In one example of IID 12, reservoir 34 may include a wall thickness, T, at closed end 34a of approximately 0.005 inches+/−0.001 inches (0.127 millimeters+/−0.0254 millimeters). In this example, protrusion 62 may be defined by a width, W, approximately equal to 0.08 inches+/−0.02 inches (2.032 millimeters+/−0.508 millimeters), a height, H, approximately equal to 0.013 inches+/−0.003 inches (0.330 millimeters+/−0.0762 millimeters), and a corner radius, R, approximately equal to 0.05 inches+/−0.006 inches (1.27 millimeters+/−0.1524 millimeters).

The number of non-contiguous protrusions that make up protrusion 62, and, thereby, the number of openings to allow access to the periphery reservoir 34 may be selected to provide a generally non-tortuous, low fluidic restriction flow path from the periphery to reservoir and pump inlets 70 and 72, respectively. In testing, a protrusion in the closed end of a bellows reservoir similar to that illustrated in FIG. 2B including three non-contiguous protrusions provided a symmetric pattern and sufficiently low fluidic restriction while not adding the cost and complexity of additional protrusions. However, in other examples, two or four or more non-contiguous protrusions may be employed in a standoff member between a reservoir and bulkhead of an IID.

The foregoing examples have been described with reference to a protrusion in the closed end of a reservoir that acts as a standoff member, which is interposed between a bulkhead and the closed end of the reservoir and which is configured to hold at least a portion of the closed end offset from the bulkhead when the reservoir is in a contracted state. Additionally, the protrusion described with reference to the examples of FIGS. 2A-4 includes a ring-shaped protrusion comprised of three non-contiguous separate protrusions. However, in other examples a standoff member in accordance with this disclosure may be different in shape and configuration, as well as placement relative to other components of an IID. For example, a standoff member in accordance with this disclosure may include a protrusion in the bulkhead of an IID that protrudes toward the closed end of the reservoir and is configured to hold at least a portion of the closed end offset from the bulkhead when the reservoir is in a contracted state. Additionally, whether arranged on the bulkhead or on the reservoir, a standoff member according to this disclosure may include protrusions in a multitude of shapes and sizes, including, e.g., a plurality of protrusions distributed over an area of the surface of the bulkhead and/or reservoir in an arbitrary pattern or a pattern other-than the ring-shaped arranged described above. In one example, standoff member configured to hold at least a portion of the closed end offset from the bulkhead when the reservoir is in a contracted state includes protrusions protruding from both the bulkhead toward the closed end of the reservoir and complementary protrusions protruding from the closed end of the reservoir toward the bulkhead.

Figure 5:
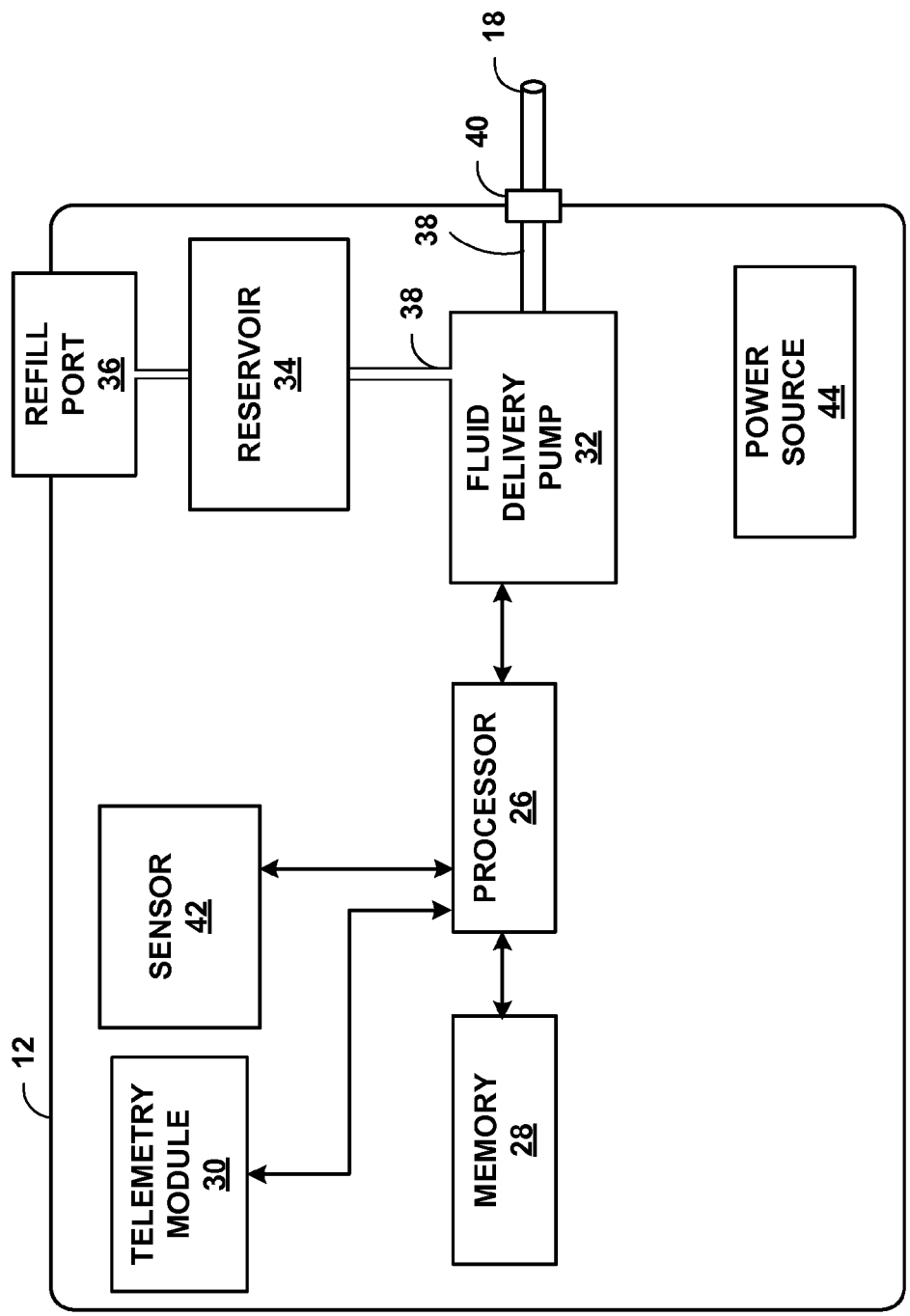
FIG. 5 is functional block diagram illustrating an example of the implantable infusion device of FIG. 1.

FIG. 5 is a functional block diagram illustrating components of an example of IID 12, which includes processor 26, memory 28, telemetry module 30, fluid delivery pump 32, reservoir 34, refill port 36, internal tubing 38, catheter access port 40, sensor 42, and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18. IID 12 also includes power source 44, which is configured to deliver operating power to various components of the IID.

In some examples, IID 12 may include a plurality of reservoirs for storing more than one type of therapeutic agent. In such cases, each of the multiple reservoirs may include a standoff member, such as protrusion 62 described above, interposed between the bulkhead and the closed end of the reservoir and configured to hold at least a portion of the closed end offset from the bulkhead when the reservoir is in a contracted state. However, for ease of description, an IID 12 including a single reservoir 34 is primarily described with reference to the disclosed examples.

As described above, during operation of IID 12, processor 26 controls fluid delivery pump 32 with the aid of instructions associated with program information that is stored in memory 28 to deliver a therapeutic agent to patient 16 via catheter 18. Instructions executed by processor 26 may, for example, define therapy programs that specify the dose of therapeutic agent that is delivered to a target tissue site within patient 16 from reservoir 30 via catheter 18. The programs may further specify a schedule of different therapeutic agent rates and/or other parameters by which IID 12 delivers therapy to patient 16. Therapy programs may be a part of a program group, where the group includes a number of therapy programs. Memory 28 of IID 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IID 12, e.g., via external programmer 20 at any time during therapy or as designated by the clinician.

Components described as processors within IID 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 28 of IID 12 may store instructions for execution by processor 26 including, e.g., therapy programs and/or program groups and any other information regarding therapy delivered to patient 16 and/or the operation of IID 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

Awareness of different properties within or related to the operation of IID 12 including, e.g., fluid flow rates, pressures, temperatures, volumes, and the like, may be desirable to monitor during operation of the device. Consequently, IID 12, in various examples, may include one or more sensor(s) 42, which may be arranged in a number of locations within IID 12, including, e.g., in reservoir 34, or a fluid pathway of the device, e.g. within a lumen of catheter 18 or refill port 36. In some examples, the sensor is configured to measure a fluid characteristic in IID 12. In some examples, the sensor may include a pressure sensor, flow sensor, pH sensor, temperature sensor or the like. In any event, IID 12 may include multiple sensors, e.g., to measure different fluid characteristics or to measure fluid characteristics in multiple locations, or to measure physiological parameters of the patient within which the device is implanted.

At various times during the operation of IID 12 to treat patient 16, communication to and from IID 12 may be necessary to, e.g., change therapy programs, adjust parameters within one or more programs, configure or adjust a particular bolus, or to otherwise download information to or from IID 12. Processor 26 controls telemetry module 30 to wirelessly communicate between IID 12 and other devices including, e.g. programmer 20. Telemetry module 30 in IID 12, as well as telemetry modules in other devices described in this disclosure, such as programmer 20, can be configured to use RF communication techniques to wirelessly send and receive information to and from other devices. In addition, telemetry module 30 may communicate with programmer 20 via proximal inductive interaction between IID 12 and the external programmer. Telemetry module 30 may send information to external programmer 20 on a continuous basis, at periodic intervals, or upon request from the programmer.

Power source 44 delivers operating power to various components of IID 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IID 12. In some examples, power requirements may be small enough to allow IID 12 to utilize patient motion and implement a kinetic energy-scavenging device to trickle charge a rechargeable battery. In other examples, traditional batteries may be used for a limited period of time. As another alternative, an external inductive power supply could transcutaneously power IID 12 as needed or desired.

Figure 6:
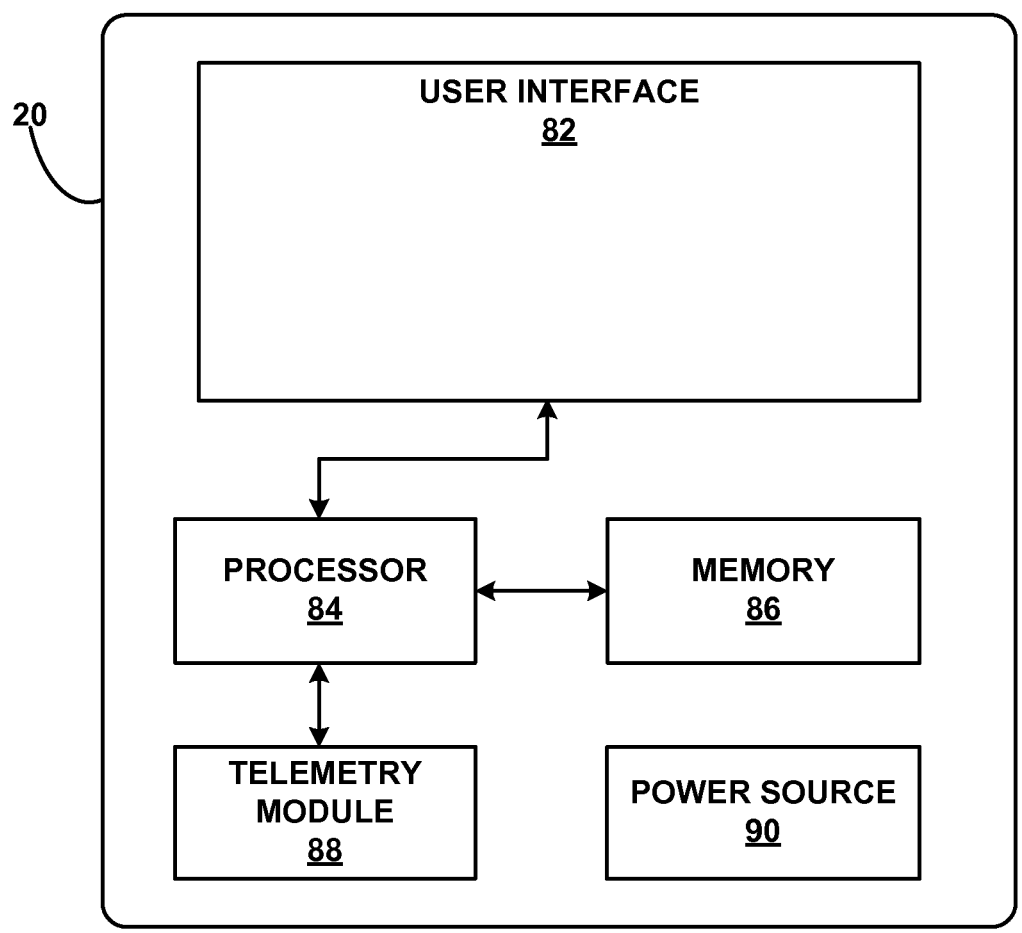
FIG. 6 is a functional block diagram illustrating an example of the external programmer of FIG. 1.

FIG. 6 is a functional block diagram illustrating an example of various components of external programmer 20 for IID 12. As shown in FIG. 6, external programmer 20 may include user interface 82, processor 84, memory 86, telemetry module 88, and power source 90. A clinician or patient 16 interacts with user interface 82 in order to manually change the parameters of a therapy program, change therapy programs within a group of programs, view therapy information, view historical or establish new therapy programs, or otherwise communicate with IID 12 or view or edit programming information. Processor 84 controls user interface 82, retrieves data from memory 86 and stores data within memory 86. Processor 84 also controls the transmission of data through telemetry module 88 to IID 12. The transmitted data may include therapy program information specifying various therapeutic agent delivery parameters. Memory 86 may store, e.g., operational instructions for processor 84 and data related to therapy for patient 16.

Programmer 20 may be a hand-held computing device that includes user interface 82 that can be used to provide input to programmer 20. For example, programmer 20 may include a display screen that presents information to the user and a keypad, buttons, a peripheral pointing device, touch screen, voice recognition, or another input mechanism that allows the user to navigate through the user interface of programmer 20 and provide input. In other examples, rather than being a handheld computing device or a dedicated computing device, programmer 20 may be a larger workstation or a separate application within another multi-function device.

User interface 82 may generally include a display screen or other output mechanisms and buttons or other input mechanisms that allow a user to receive information from and provide input to external programmer 20, respectively. In one example, user interface includes one or more of a touch pad, increase and decrease buttons, an emergency shut off button, and other buttons needed to control the therapy delivered to patient 16 by IID 12. In another example, user interface 82 may additionally or only utilize a touch screen display including, e.g., a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

Telemetry module 88 allows the transfer of data to and from programmer 20 and IID 12, as well as other devices, e.g. according to the RF communication techniques described above with reference to FIG. 2. Telemetry module 88 may communicate automatically with IID 12 at a scheduled time or when the telemetry module detects the proximity of IID 12. Alternatively, telemetry module 88 may communicate with IID 12 when signaled by a user through user interface 82. To support RF communication, telemetry module 88 may include appropriate electronic components, such as amplifiers, filters, mixers, encoders, decoders, and the like. Programmer 20 may also communicate with another programmer or computing device via a wired or wireless connection using any of a variety of communication techniques, and/or via exchange of removable media, including, e.g., magnetic or optical disks, or memory cards or sticks including, e.g., non-volatile memory. Further, programmer 20 may communicate with IID 12 or another device via, e.g., a local area network (LAN), wide area network (WAN), public switched telephone network (PSTN), or cellular telephone network, or any other terrestrial or satellite network appropriate for use with programmer 20 and IID 12.

Power source 90 may be a rechargeable battery, such as a lithium ion or nickel metal hydride battery. Other rechargeable or conventional primary cell batteries may also be used. In some cases, external programmer 20 may be used when coupled to an alternating current (AC) outlet, i.e., AC line power, either directly or via an AC/DC adapter.

In some examples, external programmer 20 may be configured to recharge IID 12 in addition to programming IID 12. Alternatively, a recharging device may be capable of communication with IID 12. Then, the recharging device may be able to transfer programming information, data, or any other information described herein to IID 12. In this manner, the recharging device may be able to act as an intermediary communication device between external programmer 20 and IID 12.

The techniques described in this disclosure associated with control electronics of an IID or external device, such as an external programmer may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Examples according to this disclosure provide techniques for reducing the accumulation of gases in an IID by facilitating proper purging of the device during an initial purge and prime procedure before implantation within a patient or subsequent refill procedures post implantation. In examples according to this disclosure, an IID includes a standoff member that is interposed between a bulkhead and one end of a reservoir, which is configured to hold at least a portion of the end of the reservoir offset from the bulkhead when the reservoir is in a contracted state. The standoff member creates an open space in the reservoir, which is maintained during a purge and prime and/or refill procedure and which defines a fluid path between an inlet of the reservoir from a refill port to an inlet of the pump of the IID. The open fluid path maintained by the standoff member facilitates purging gases from the IID downstream of and within the pump during an initial purge and prime procedure following manufacture of the device and during subsequent refill procedures. Examples according to this disclosure may function to reduce the effects of gas accumulation within an IID, including, e.g., reducing the effect of gas accumulation on the operation of the IID, e.g. the ability of the pump to accurately deliver metered fluid doses to a patient. Additionally, examples according to this disclosure may function to reduce the effects of gas accumulation within the reservoir of the IID, e.g. reduce adverse effects of gas accumulation on some therapeutic agents stored within the reservoir over time.

Various examples have been described. These and other examples are within the scope of the following claims.

The invention claimed is:

1. An implantable infusion device (IID) comprising:
   a housing;
   an expandable and contractible reservoir configured to store a therapeutic agent and arranged within the housing, wherein a first end of the reservoir is configured to move with respect to the housing and collapse toward a second end of the reservoir as the reservoir contracts, and wherein the first end of the reservoir and the second end of the reservoir are configured to contact the therapeutic agent, and wherein the reservoir defines an inlet through which the therapeutic agent is received and an outlet through which the therapeutic agent exits the reservoir, the inlet being different than the outlet; and
   a standoff member interposed between the first end and the second end of the reservoir, wherein the standoff member is configured to hold at least a portion of the first end offset from the second end and maintain a flow path between the inlet and the outlet when the reservoir is in a contracted state, and wherein the first end of the reservoir comprises the standoff member.

2. The IID of claim 1, wherein the standoff member comprises a protrusion in the first end of the reservoir protruding toward the second end of the reservoir.

3. The IID of claim 2, wherein the reservoir comprises a corrugated annular side connected to the first end and the second end of the reservoir and configured to expand and contract to change a distance between the first end and the second end of the reservoir.

4. The IID of claim 3, wherein the first end is substantially planar and the annular side of the reservoir is arranged substantially perpendicular to the first end such that the reservoir comprises a cylindrical expandable and contractible reservoir.

5. The IID of claim 4, wherein each of the first end and the second end of the reservoir is at least one of circular, rectangular, or elliptical.

6. The IID of claim 2, wherein the protrusion comprises a ring-shaped protrusion generally aligned with a center of the first end.

7. The IID of claim 6, wherein the ring-shaped protrusion comprises a diameter selected based on a location of at least one of the inlet of the reservoir and an inlet to a pumping mechanism of the IID, the inlet to the pumping mechanism corresponding to the outlet of the reservoir.

8. The IID of claim 7, wherein the diameter of the ring-shaped protrusion is selected such that a space formed by the portion of the first end offset from the second end when the reservoir is in the contracted state creates the flow path between the inlet of the reservoir and the inlet to the pumping mechanism.

9. The IID of claim 6, wherein the ring-shaped protrusion comprises a height selected based on a size of the flow path created by the portion of the first end offset from the second end when the reservoir is in the contracted state.

10. The IID of claim 9, wherein the height of the ring-shaped protrusion is greater than or equal to a target fluidic resistance of the flow path.

11. The IID of claim 10, wherein the target fluidic resistance is greater than a fluidic resistance of a needle employed to at least one of purge, prime, or refill the reservoir.

12. The IID of claim 6, wherein the ring-shaped protrusion comprises a plurality of non-contiguous protrusions that form a ring comprising a center generally aligned with a center of the first end of the reservoir.

13. The IID of claim 12, wherein the non-contiguous protrusions comprise three non-contiguous protrusions that form the ring comprising the center generally aligned with the center of the first end of the reservoir.

14. The IID of claim 1, wherein the housing comprises:
   a housing shield;
   a bulkhead connected to the housing shield such that the housing shield and the bulkhead form a substantially closed housing chamber within which the reservoir is arranged,
   wherein the second end of the reservoir is connected to the bulkhead such that the first end of the reservoir is configured to collapse toward the bulkhead as the reservoir contracts, and the standoff member is configured to hold at least a portion of the first end offset from the bulkhead when the reservoir is in the contracted state.

15. The IID of claim 14, wherein the standoff member comprises at least one protrusion in the bulkhead protruding toward the first end of the reservoir.

16. An implantable infusion device (IID) comprising:
a housing;
an expandable and contractible reservoir configured to store a therapeutic agent and arranged within the housing, the reservoir comprising:
a first end connected to the housing;
a substantially closed second end comprising a protrusion protruding toward the first end; and
a side connecting the first and the second ends to form a reservoir chamber within
which the reservoir stores the therapeutic agent,
wherein the second end of the reservoir is configured to move with respect to the housing and collapse toward the first end as the reservoir contracts,
wherein the first end of the reservoir and the second end of the reservoir are configured to contact the therapeutic agent,
wherein the reservoir defines an inlet through which the therapeutic agent is received and an outlet through which the therapeutic agent exits the reservoir, the inlet being different than the outlet, and
wherein the protrusion is configured to hold at least a portion of the second end offset from the first end and maintain a flow path between the inlet and the outlet when the reservoir is in a contracted state.

17. The IID of claim 16, wherein the second end is substantially planar and the side of the reservoir is a corrugated annular side substantially perpendicular to the second end such that the reservoir comprises a cylindrical expandable and contractible reservoir.

18. The IID of claim 17, wherein each of the first end and the second end of the reservoir is at least one of circular, rectangular, or elliptical.

19. The IID of claim 16, wherein the protrusion comprises a ring-shaped protrusion generally aligned with a center of the second end.

20. The IID of claim 19, wherein the ring-shaped protrusion comprises a diameter selected based on a location of at least one of the inlet of the reservoir and an inlet to a pumping mechanism of the IID, the inlet to the pumping mechanism corresponding to the outlet of the reservoir.

21. The IID of claim 20, wherein the diameter of the ring-shaped protrusion is selected such that a space formed by the portion of the second end offset from the first end when the reservoir is in the contracted state creates the flow path between the inlet of the reservoir and the inlet to the pumping mechanism.

22. The IID of claim 19, wherein the ring-shaped protrusion comprises a height selected based on a size of the flow path created by the portion of the second end offset from the first end when the reservoir is in the contracted state.

23. The IID of claim 22, wherein the height of the ring-shaped protrusion is greater than or equal to a target fluidic resistance of the flow path.

24. The IID of claim 23, wherein the target fluidic resistance is greater than a fluidic resistance of a needle employed to at least one of purge, prime, or refill the reservoir.

25. The IID of claim 19, wherein the ring-shaped protrusion comprises a plurality of non-contiguous protrusions that form a ring comprising a center generally aligned with a center of the second end.

26. The IID of claim 25, wherein the non-contiguous protrusions comprise three non-contiguous protrusions that form the ring comprising the center generally aligned with the center of the second end.

27. The IID of claim 16, wherein the housing comprises:
a housing shield;
a bulkhead connected to the housing shield such that the housing shield and the bulkhead form a substantially closed housing chamber within which the reservoir is arranged,
wherein the first end of the reservoir is connected to the bulkhead such that the second end of the reservoir is configured to collapse toward the bulkhead as the reservoir contracts and the protrusion is configured to hold at least a portion of the second end offset from the bulkhead when the reservoir is in the contracted state.

28. A reservoir configured to store a therapeutic agent in an implantable infusion device (IID), the reservoir comprising:
a first end comprising a ring-shape that forms an opening toward a center of the first end;
a second substantially closed planar end comprising a protrusion protruding toward the first end, wherein the second end is configured to move with respect to a housing of the IID, and wherein the first end and the second end are configured to contact the therapeutic agent; and
a corrugated annular side substantially perpendicular to the first and the second ends and connecting the first and the second ends to form a cylindrical chamber within which the reservoir stores the therapeutic agent,
wherein the corrugated annular side is configured to expand and contract to change a distance between the first end and the second end of the reservoir,
wherein the reservoir defines an inlet through which the therapeutic agent is received and an outlet through which the therapeutic agent exits the reservoir, the inlet being different than the outlet, and
wherein the protrusion is configured to hold at least a portion of the second end offset from the first end and maintain a flow path between the inlet and the outlet when the reservoir is in a contracted state.

29. An implantable infusion device (IID) comprising:
a housing;
an expandable and contractible reservoir configured to store a therapeutic agent and arranged within the housing, wherein a first end of the reservoir is configured to move with respect to the housing and collapse toward a second end of the reservoir as the reservoir contracts, and wherein the first end of the reservoir and the second end of the reservoir are configured to contact the therapeutic agent, and wherein the reservoir defines an inlet through which the therapeutic agent is received and an outlet through which the therapeutic agent exits the reservoir, the inlet being different than the outlet; and
a standoff means interposed between the first end and the second end of the reservoir, wherein the standoff means is for holding at least a portion of the first end offset from the second end and maintain a flow path between the inlet and the outlet when the reservoir is in a contracted state, and wherein the first end of the reservoir comprises the standoff means.

* * * * *